United States Patent
Kim

(10) Patent No.: US 9,909,859 B2
(45) Date of Patent: Mar. 6, 2018

(54) APPARATUS AND METHOD FOR MEASURING VISUAL RANGE USING GEOMETRICAL INFORMATION OF AN IMAGE AND AN IMAGE PATTERN RECOGNITION TECHNIQUE

(71) Applicant: Body for Gyeongju Univ. Education & Industry Cooperation, Gyeongju-si (KR)

(72) Inventor: Kyung Won Kim, Daegu-si (KR)

(*) Notice: Subject to any disclaimer, the term of this patent is extended or adjusted under 35 U.S.C. 154(b) by 505 days.

(21) Appl. No.: 14/566,712

(22) Filed: Dec. 11, 2014

(65) Prior Publication Data

US 2015/0285624 A1   Oct. 8, 2015

(30) Foreign Application Priority Data

Apr. 4, 2014 (KR) .................. 10-2014-0040784

(51) Int. Cl.

| | | |
|---|---|---|
| H04N 9/47 | (2006.01) | |
| H04N 7/18 | (2006.01) | |
| G01B 11/14 | (2006.01) | |
| H04N 5/232 | (2006.01) | |
| H04N 9/07 | (2006.01) | |
| G06T 7/73 | (2017.01) | |
| G01N 21/53 | (2006.01) | |

(52) U.S. Cl.
CPC ............ *G01B 11/14* (2013.01); *G06T 7/73* (2017.01); *H04N 5/23203* (2013.01); *H04N 9/07* (2013.01); *G01N 21/538* (2013.01); *G06T 2207/10024* (2013.01); *G06T 2207/10032* (2013.01)

(58) Field of Classification Search
CPC ...... G01B 11/14; G06T 7/73; H04N 5/23203; H04N 9/07
USPC ........................................... 348/140
See application file for complete search history.

(56) References Cited

U.S. PATENT DOCUMENTS

2010/0080448 A1* 4/2010 Tam .................. G06T 7/50
382/154

FOREIGN PATENT DOCUMENTS

| KR | 10-2006-0046276 | | 5/2007 |
|---|---|---|---|
| KR | 10-0751494 | | 8/2007 |
| KR | 10-2006-0046276 | * | 5/2010 |
| KR | 10-0958210 | * | 5/2010 |

(Continued)

OTHER PUBLICATIONS

English translation of 10-0751494.
(Continued)

*Primary Examiner* — Mehrdad Dastouri
*Assistant Examiner* — Kristin Dobbs
(74) *Attorney, Agent, or Firm* — Antonio Ha & U.S. Patent, LLC

(57) ABSTRACT

The present invention relates to a measurement system for calculating visual range using perspective and geometrical information of an image captured by a camera, CCTV, camcorder, or other imaging device and a method for measuring visual range from a non-linear function through pattern recognition on an image. The present measurement system and method may make up for uncertainty due to assumption that aerosol is evenly distributed and limit to measurement space in the optimal measurement method, thus offering more objective data.

4 Claims, 8 Drawing Sheets

(56) References Cited

FOREIGN PATENT DOCUMENTS

| KR | 10-1032160 | 5/2011 |
|----|------------|--------|
| KR | 10-1283400 | 7/2013 |

OTHER PUBLICATIONS

English translation of 10-2006-0046276.
English translation of 10-0958210.
English translation of 10-1032160.
English translation of 10-1283400.

* cited by examiner

Fig. 6

APPARATUS AND METHOD FOR MEASURING VISUAL RANGE USING GEOMETRICAL INFORMATION OF AN IMAGE AND AN IMAGE PATTERN RECOGNITION TECHNIQUE

CROSS-REFERENCE TO RELATED APPLICATIONS

This patent application claims priority under 35 U.S.C. § 119 to Korean Patent Application No. 10-2014-0040784, filed on Apr. 4, 2014, in the Korean Intellectual Property Office, the disclosure of which is incorporated by reference herein in its entirety.

TECHNICAL FIELD

Embodiments of the present invention relate to a system and theoretical method for measuring a visual range through geometrical information of an image captured through an imaging apparatus, such as a camera, CCTV, or camcorder, and perspective.

DISCUSSION OF RELATED ART

Visibility, which is farthest distance human can see, is recorded as visual range. A visual range may be measured in a visual, optical, or imaging manner. A visual range serves as an index that enables quantitative evaluation of air pollution and this range also functions to prevent economic loss from occurring due to poor visibility in the airport, road, or sea. Accordingly, a need exists for a measuring system with enhanced accuracy and reproducibility in visual range measurement through an analysis algorithm that may measure a visual range by reflecting the actual distance of an object.

A visual range may be measured or recorded by naked eye observation. Naked eye observation refers to a method in which a skilled observer observes an object within his visibility in all directions based on the distance from the object. Visibility depends on gaseous or particulate matters in the ambient air within the observer's view angle. In addition, visibility may be increased or decreased depending on variations in meteorological elements (relative humidity, precipitation, etc.) that may cause light extinction or concentration of air pollutants. A recent visual range measurement method is to utilize a forward scattering meter that may measure the amount of light scattered by gaseous and particulate matters in the ambient air to estimate meteorological-optical visibility. The forward scattering meter estimates visibility by detecting light attenuation of aerosol, but the meter does not reflect an amount of light absorption. Accordingly, the visual range measured by the forward scattering meter contains theoretical errors, and the meter is vulnerable to visibility changes due to precipitation. Various visual range measurement techniques using images captured using a camera are nowadays being introduced. However, such techniques require a separate auxiliary facility or target to be installed, and sensitively react with various configurations of variables in the analysis step. Further, the techniques were not verified for the visual range of 10 km or more. Still further, they calculate a visual range using brightness and illumination intensity of an image without considering actual distance to their analytic algorithm for quantifying a visual range, thus it is difficult to evaluate its measurement accuracy for a long visual range.

The present invention was funded by the Korea Meteorological Administration Research and Development Program under Grant KMIPA 2013-22110.

SUMMARY

An embodiment of the present invention provides an apparatus and method for measuring a visual range from a measurement site, where an IP camera is installed, by remotely transmitting an image captured using the IP camera to the monitoring center. This visual range defined as an image visual range.

An embodiment of the present invention provides an apparatus and method for measuring a visual range using a method for inputting geometrical information of an image.

An embodiment of the present invention provides an apparatus and method for measuring a visual range using a method for determining an image visual range function.

An embodiment of the present invention provides an apparatus and method for measuring a visual range that may measure the distance of a recognizable object by identifying the object using an image pattern recognition method.

The present invention is not limited to the foregoing objects, and other unmentioned objects will be apparent to one of ordinary skill in the art from the following description.

According to an embodiment of the present invention, a visual range measurement apparatus using geometrical information of an image and an image pattern recognition technique comprises an IP camera installed to transmit an image of a measurement site, an image storing unit configured to selectively extract a still image from a video image of the transmitted image, and a visual range calculation unit configured to recognize a coordinate of a similar color region from the image visual range function and the geometrical information of the image and to calculate a visual range.

According to an embodiment of the present invention, a visual range measurement method using geometrical information of an image and an image pattern recognition technique comprises receiving an image from an IP camera installed at a measurement site, performing distance-mapping on the analytic region of the received image, determining an image visual range function from the received image, applying an image pattern recognition method using ambient color information of an object from the received image, and calculating a visual range from a coordinate calculated by the image pattern recognition method.

Details of other embodiments are set forth in the detailed description and the drawings.

Advantages and features of the present invention, and methods for achieving the same may be understood through the embodiments to be described below taken in conjunction with the accompanying drawings. However, it should be appreciated that the present invention is not limited to particular embodiments and various changes or modifications may be made thereto without departing from the spirit and scope of the present invention. The embodiments set forth herein are provided for thorough disclosure of the present invention and making the category of the present invention known to one of ordinary skill in the art, and the present invention is defined only by the claims. The same reference numerals may refer to the same or similar elements throughout the specification and the drawings.

An embodiment of the present invention may enhance uncertainty of visual range measurement, which is an issue from the conventional visual, optical, and imaging observation technologies. A visual range may be more accurately measured by capturing a visual range as an image using an IP camera and adopting actual geometrical information of the object and an image pattern recognition method.

An embodiment of the present invention may make up for the issues such as measurement errors that may occur as the conventional forward-scattering measurement method does not consider a light absorption amount, subject determination on visual range recognition of a target object, which is a drawback of the conventional visual measurement method, and a need of installing an auxiliary means and inaccuracy due to lack of distance information in the imaging observation method, thus enhancing accuracy in visual range measurement.

An embodiment of the present invention allows for measurement at lower costs as compared with the optical observation method and simultaneous monitoring and recording of a visual range in more sites as compared with the visual measurement method.

An embodiment of the present invention may leave actual images unlike the conventional optical and visual measurement methods provide only numeric values, thus providing for increased reliability.

BRIEF DESCRIPTION OF DRAWINGS

A more complete appreciation of the present disclosure and many of the attendant aspects thereof will be readily obtained as the same becomes better understood by reference to the following detailed description when considered in connection with the accompanying drawings, wherein:

FIG. 6 is a view illustrating a correction factor of an image visual range for a coordinate visual range efficiency coefficient α and a perspective coefficient β according to an embodiment of the present invention;

DETAILED DESCRIPTION OF EMBODIMENTS

A visual range measurement apparatus using an image according to an embodiment of the present invention is subjected to an installation step and an operation step. In the installation step, an IP camera is installed in a place where an object remotely identifiable from a long distance is viewed. After installation, the IP camera is fixed. In the operation step, an analytic region is set in an image transmitted from a measurement site, geometrical information is input to determine an image visual range function, and a visual range is then computed by a pattern recognition method. The visual range is indicated as an image visual range.

According to an embodiment of the present invention, results may offer various embodiments depending on image obtaining conditions. Some embodiments of the present invention are hereinafter described with reference to the accompanying drawings, but the present invention is not limited thereto.

It will be understood that when an element or layer is referred to as being "on," "connected to," "coupled to," or "adjacent to" another element or layer, it can be directly on, connected, coupled, or adjacent to the other element or layer, or intervening elements or layers may be present. As used herein, the singular forms "a," "an," and "the" are intended to include the plural forms as well, unless the context clearly indicates otherwise.

Hereinafter, embodiments of the present invention are described in detail with reference to the accompanying drawings.

Figure 1:
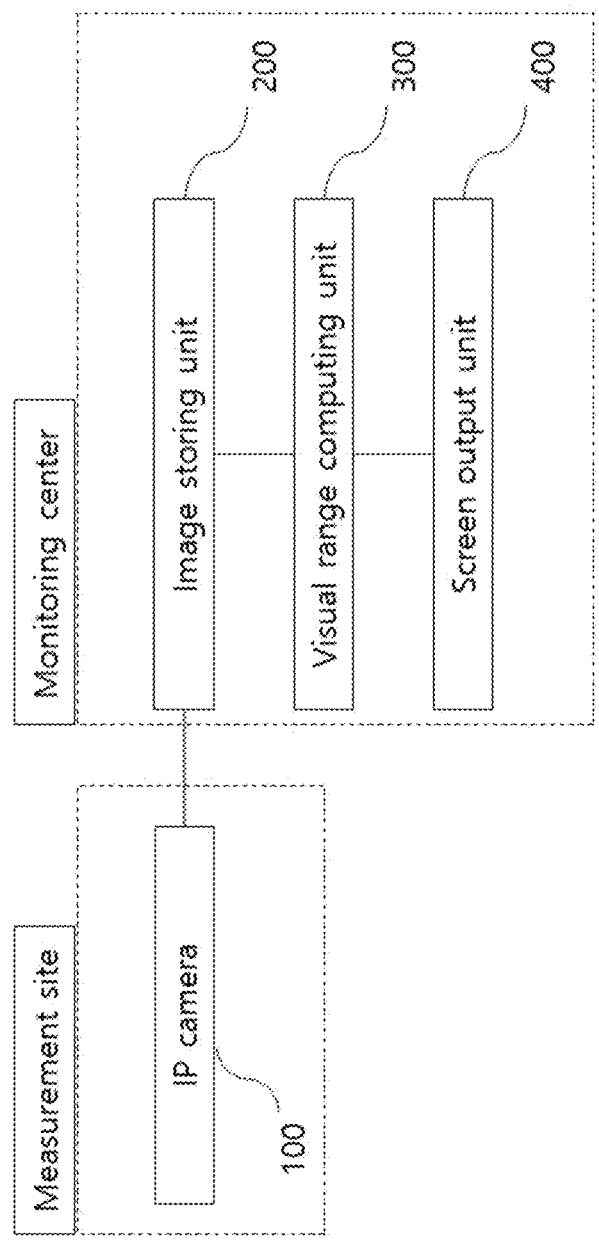
FIG. 1 is a concept view illustrating a visual range measurement apparatus according to an embodiment of the present invention.
Figure 2:
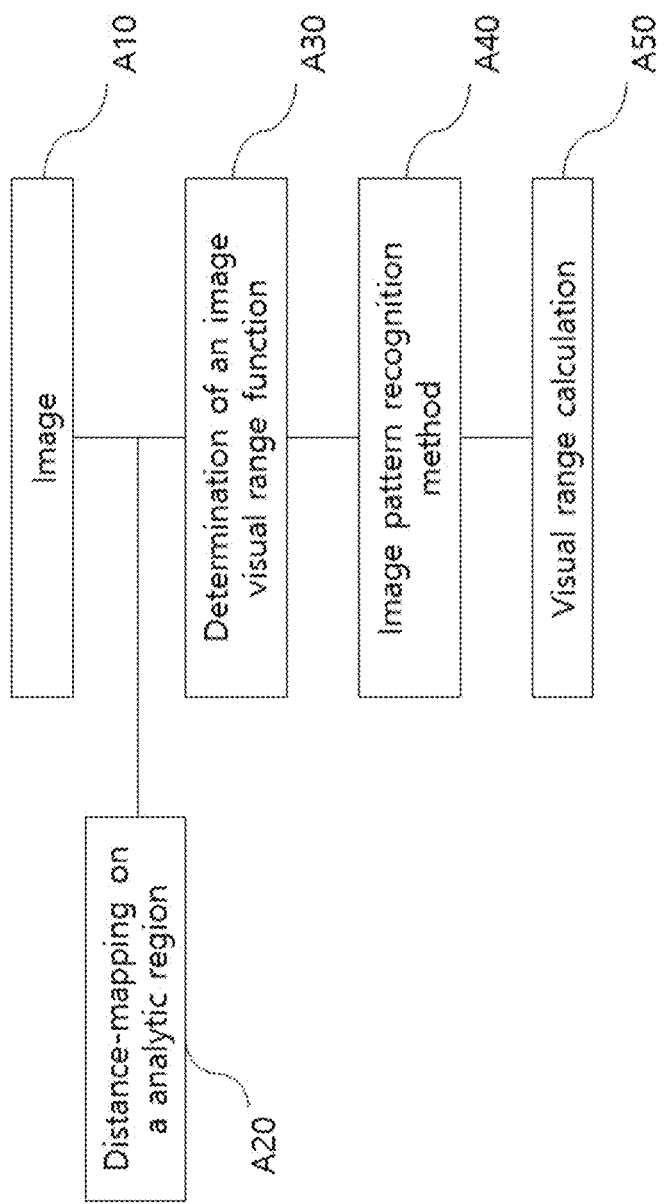
FIG. 2 is a flowchart illustrating a visual range measurement method according to an embodiment of the present invention.

FIG. 1 is a concept view illustrating a visual range measurement apparatus according to an embodiment of the present invention. FIG. 2 is a flowchart illustrating a visual range measurement method according to an embodiment of the present invention. According to an embodiment of the present invention, a visual range measurement apparatus and method are described with reference to FIGS. 1 and 2.

Referring to FIG. 1, according to an embodiment of the present invention, the visual range measurement apparatus includes an IP camera 100, an image storing unit 200, a visual range computing unit 300, and a screen output unit 400.

The IP camera 100 selects a measurement site that may represent visibility of a target area, captures a color image, and remotely transmits the image to the image storing unit 200 positioned in a monitoring center (A10). Here, the target area refers to an area where a long visual range may be measured. The IP camera 100 may refer to any device that, such as a CCD (Charge-Coupled Device) or CMOS (Complementary Metal-Oxide Semiconductor), may capture an image and that may be assigned an IP (Internet Protocol) address or domain address to transmit the image to a remote site.

The image storing unit 200 may refer to any device that may store the image transmitted from the IP camera 100 in, e.g., a hard disc, in an electronic video file, and that may selectively extract a still image from the stored video image and transmit the extracted image to the visual range computing unit 300.

FIG. 2 is a flowchart illustrating a visual range measurement method by a visual range computing unit 300 according to an embodiment of the present invention. The image (A10) received and obtained from the remote monitoring site undergoes distance-mapping on the analytic region (A20), determination of an image visual range function (A30), an image pattern recognition method (A40), and visual range calculation (A50), thereby producing a visual range.

Figure 3:
FIG. 3 is a view illustrating a captured image according to an embodiment of the present invention.

FIG. 3 is a view illustrating a captured image according to an embodiment of the present invention. The visual range computing unit 300 investigates the image A10 received from the image storing unit 200 shown in FIG. 3 and selects an analytic region for measuring a visual range.

Figure 4:
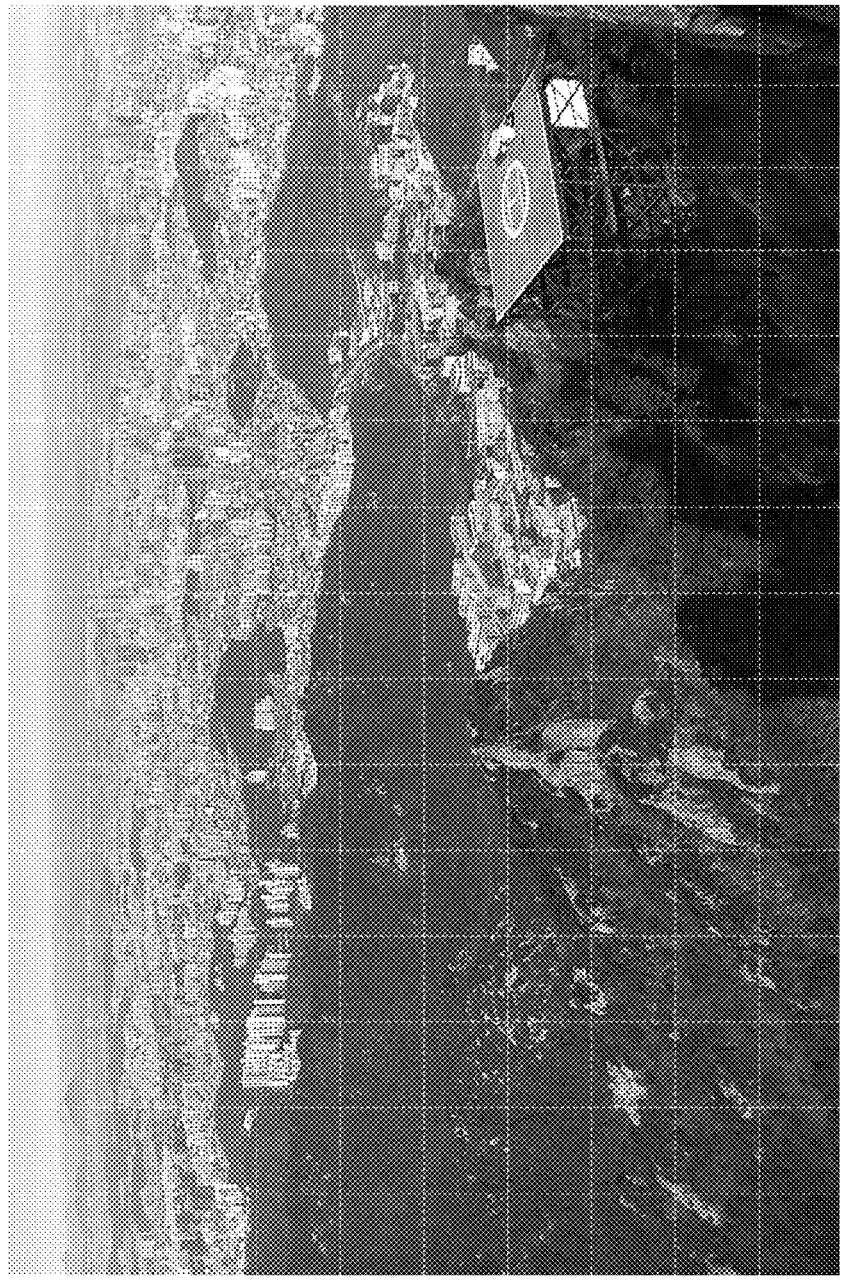
FIG. 4 is a view illustrating an image that has undergone distance-mapping on the analytic region of the received image according to an embodiment of the present invention.

FIG. 4 is a view illustrating an image that has undergone distance-mapping on the analytic region of the image according to an embodiment of the present invention. The analytic region selected from the image A10 is subjected to distance-mapping on the analytic region A20 using geometrical information of the captured area as shown in FIG. 4. A distance for a 2D (two dimensional) plane coordinate in the selected analytic region of the image is expressed and processed as in Equation 1:

$$f(x,y)=d \quad \text{[Equation 1]}$$

where, d refers to the distance at a given coordinate.

Distance per y-coordinate calculated by the distance-mapping on the analytic region (A20) are utilized in the step of the determination of an image visual range function (A30) as shown in FIG. 2. A visual range is expressed and processed with respect to the distances per y-coordinate as in Equation 2:

$$IVR=f(y)+d_0 \quad \text{[Equation 2]}$$

where, IVR refers to an image visual range, f(y) an image visual range function, and do a zero distance. The image visual range is calculated by summing the image visual range function and the zero distance. The zero distance refers to a distance at coordinate (x,0). The image visual range function that is a function of distance with respect to y coordinate is expressed and processed as in Equation 3:

$$f(y)=\alpha \times [\{1-y/(y\max+f/d\max)\}^{-\beta}-1] \quad \text{[Equation 3]}$$

where, $\alpha$ is a coordinate visual range efficiency coefficient, and $\beta$ is a perspective coefficient. The coordinate visual range efficiency coefficient and the perspective coefficient are adjusted based on the distance per y-coordinate calculated by performing distance-mapping on the analytic region of the image to determine the coordinate visual range efficiency coefficient and the perspective coefficient so that the image visual range most complies with the distance per y-coordinate.

Here, $d_{max}$ is the distance per y-coordinate of an object positioned furthermost in the analytic region of the image, and f is a correction factor of an image visual range. According to an embodiment of the present invention, an example is described in which the determination of an image visual range function (A30) applies to the visual range measuring apparatus using an image.

Figure 5:
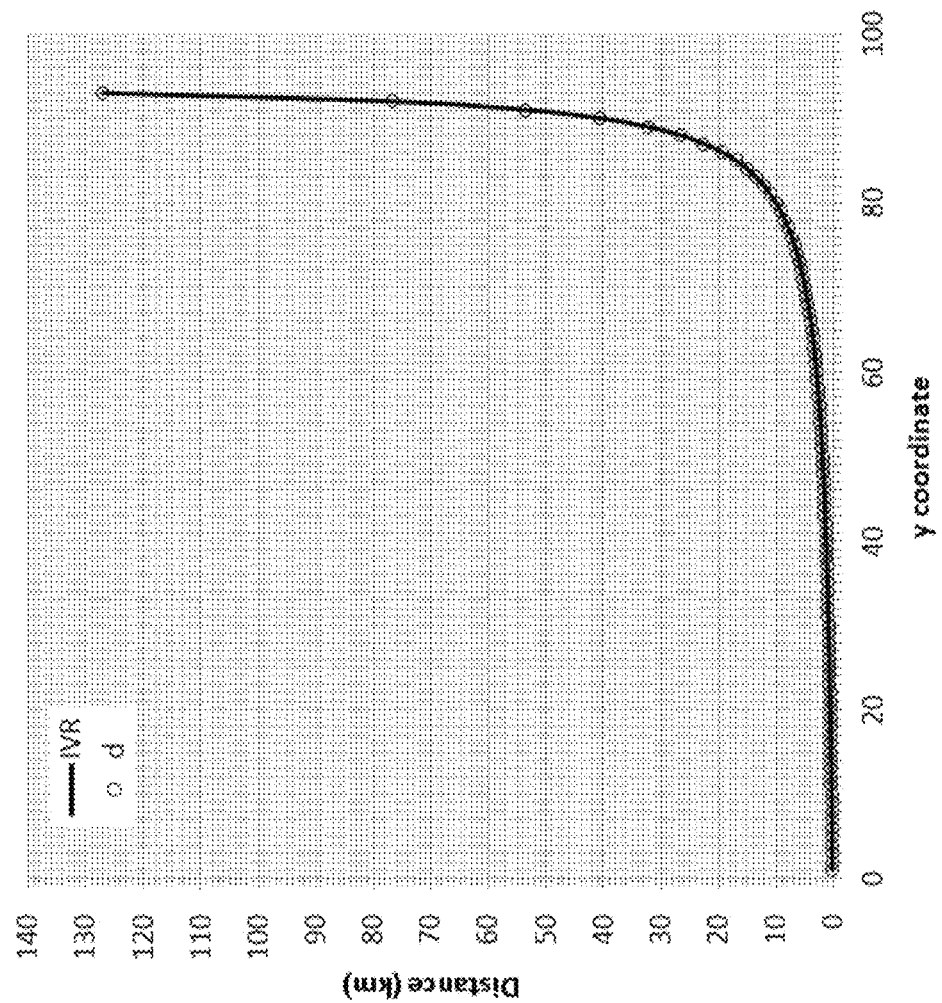
FIG. 5 is a view illustrating actual distances (d) per y-coordinate and an image visual range (IVR) per y-coordinate according to an embodiment of the present invention.

FIG. 5 is a view illustrating relationship between a distance per y-coordinate (d) and an image visual range (IVR) according to an embodiment of the present invention. Referring to FIG. 5, distances per y-coordinate which are calculated by performing distance-mapping on the analytic region of the image are shown.

Figure 6:
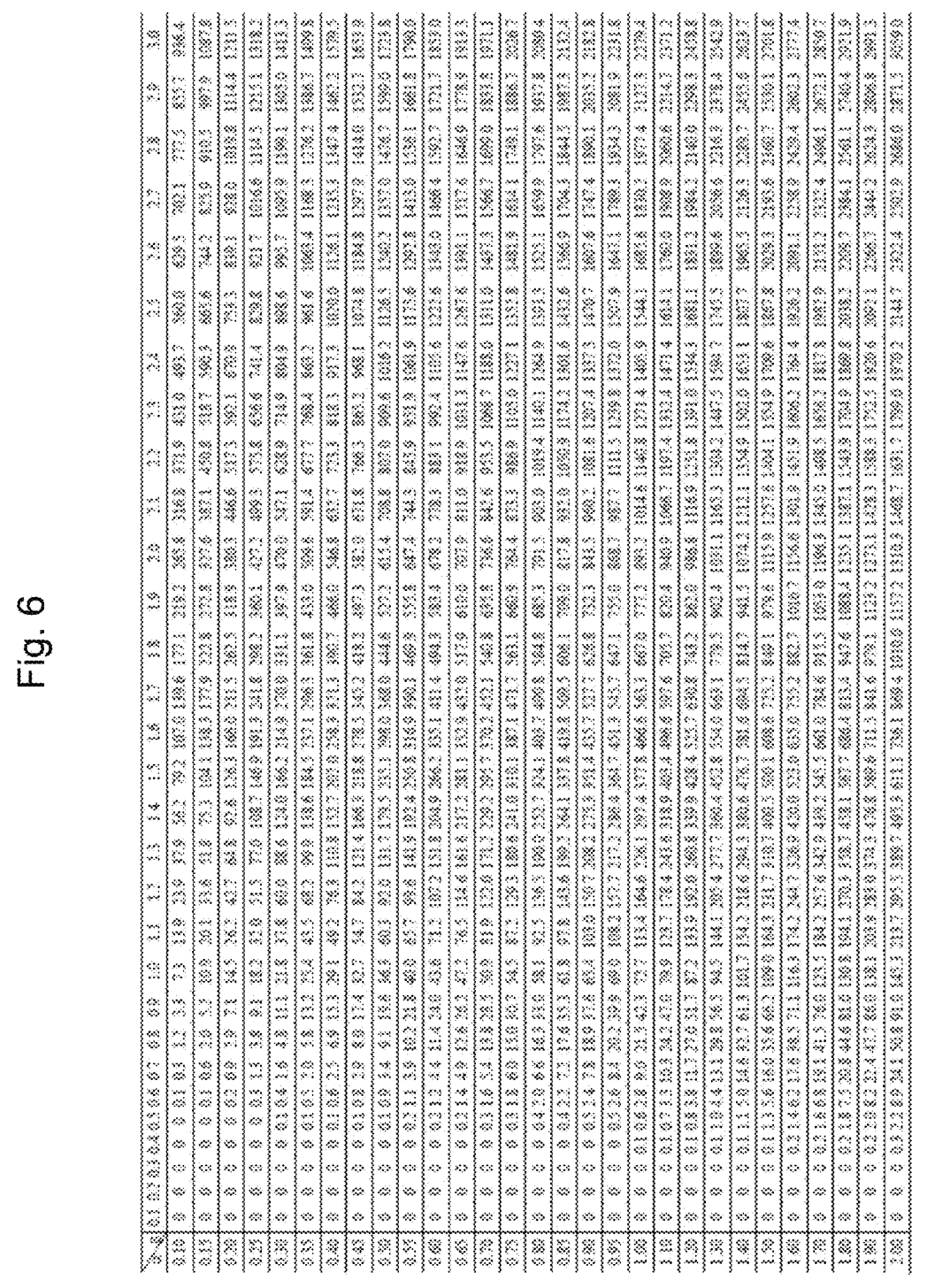

FIG. 6 is a view illustrating correction factors of an image visual range for coordinate visual range efficiency coefficients $\alpha$ and perspective coefficients $\beta$ according to an embodiment of the present invention.

Referring to FIG. 5, the image visual range function that most complies with the distance per y-coordinate calculated by performing distance-mapping on the analytic region of the image is obtained when the coordinate visual range efficiency coefficients is 1.2, and the perspective coefficient is 1.2. In this case, referring to FIG. 6, the correction factors of the image visual range is determined to be 192.0. According to an embodiment of the present invention, in the step of distance-mapping on the analytic region (A20), $d_{max}$ is 127 km.

Accordingly, the image visual range function A30 may be determined from the determined the coordinate visual range efficiency coefficient, the perspective coefficient, the correction factors of the image visual range, and the distance per y-coordinate of an object positioned furthermost in the analytic region of the image.

Figure 7:
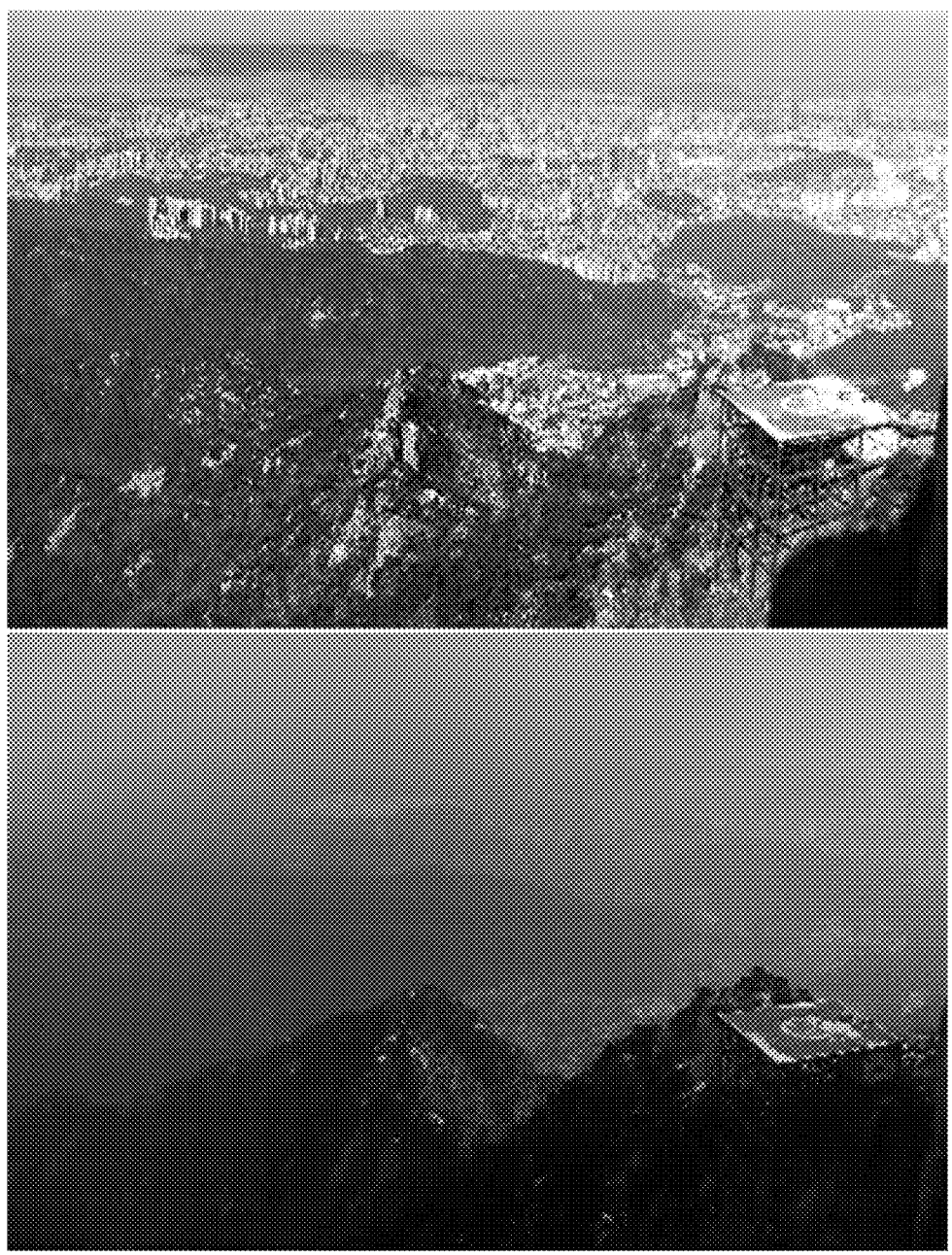
FIG. 7 is a view illustrating an exemplary image analyzed by an image pattern recognition method according to an embodiment of the present invention.

FIG. 7 is a view illustrating an exemplary image analyzed by an image pattern recognition method according to an embodiment of the present invention.

The image pattern recognition method utilizes RGB color information. An ambient color of an object viewed farthest in the analytic region of the image is selected as a reference color. The RGB values of the reference color are extracted, and a similar color tolerance range is set. Similar colors in the tolerance range for the RGB values of the reference color may be connected to one another to determine an ambient color region of the object viewed farthest in the analytic region of the image.

Referring to FIG. 7, the upper image of FIG. 7 is observed further than the lower image of FIG. 7. It can be seen from FIG. 7 that an ambient color region of an object viewed farthest in the upper image is shown to be different from that in the lower image.

In the visual range calculation step (A50), coordinates to be applied to the image visual range function are input from the RGB values per coordinate of the color region determined by the image pattern recognition method. In Equation 3 above, the minimum coordinate value of the color region is input as y coordinate to thereby calculate a visual range.

Figure 8:
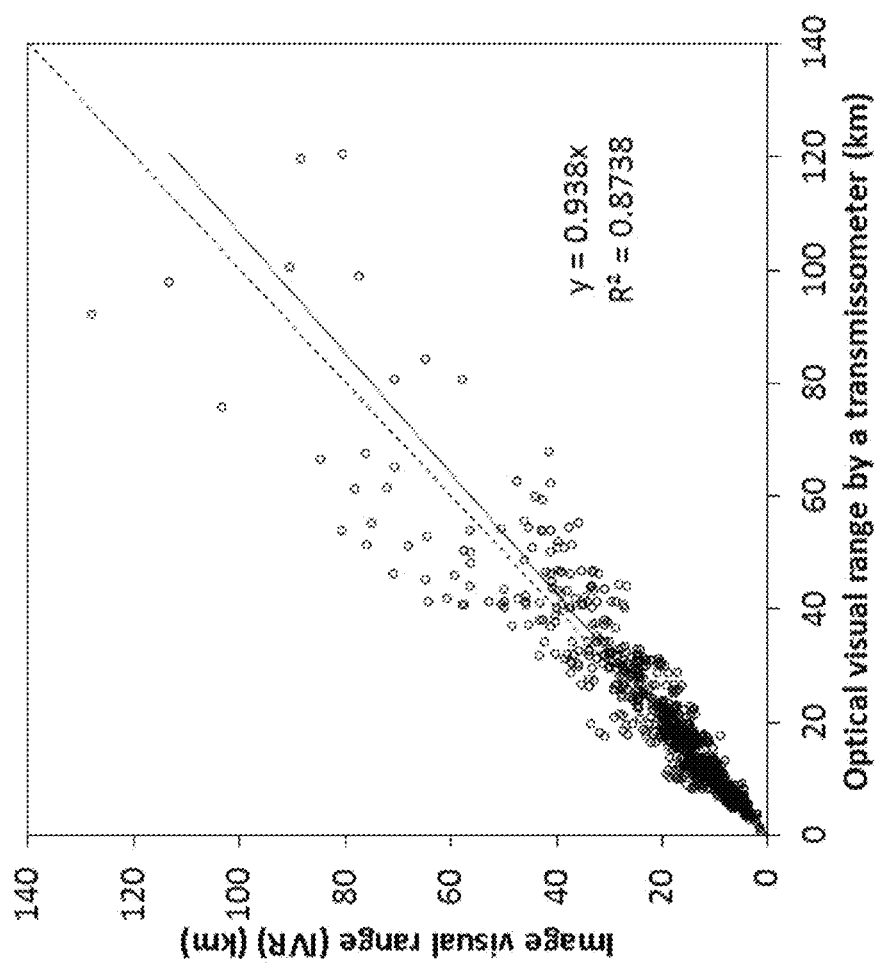
FIG. 8 is a scatter plot illustrating comparison between an image visual range and visual range measured using a transmissometer, which is an optical visual range measurement, according to an embodiment of the present invention.

FIG. 8 is a scatter plot illustrating comparison between an image visual range and visual range measured using a transmissometer, which is an optical visual range measurement, according to an embodiment of the present invention.

Referring to FIG. 8, a slope is 0.938 and a correlation is 0.8738 between the visual range (image visual range) calculated by the step of distance-mapping on the analytic region (A20), the step of the determination of an image visual range function (A30), the image pattern recognition method step (A40), and the visual range calculation step (A50) and the visual range (optical visual range) measured by a transmissometer (not shown) which is an optical visual range measurement. Accordingly, it can be identified that the visual range calculated according to an embodiment of the present invention shows good correlation with the visual range measured by the transmissometer (not shown).

The screen output unit 400 may display the image on the screen or store the image, may display the image color information per coordinate calculated in the image pattern recognition method (A40) in RGB and store the image color information per coordinate, and may display and store the visual range obtained from the visual range calculation unit 300.

Embodiments of the present invention may be stored in a computer-readable medium that contains programming commands implementable by various computers. The computer-readable medium may include programming commands, local data files, local data structures, alone or in combinations thereof. The medium may be one that may be specially manufactured for the present invention or that may be known and available to one of ordinary skill in the computer software-related art.

Although the present invention has been shown and described in connection with embodiments thereof, it should be understood that various changes in form and detail may be made thereto without departing from the scope of the present invention defined in the following claims.

The invention claimed is:

1. An apparatus for measuring a visual range using geometrical information of an image and an image pattern recognition method, the apparatus comprising:
an IP camera installed to transmit an image of a measurement site;

an image storing unit selectively extracting a still image from a video image of the transmitted image; and a visual range computing unit recognizing a coordinate of a similar color region from an image visual range function and the geometrical information of the image, performs distance-mapping on an analytic region of the image received from the IP camera, determines the image visual range function from a zero distance, a coordinate visual range efficiency coefficient, a perspective coefficient, a correction factor of an image visual range, and a distance per y-coordinate of an object positioned furthermost in the analytic region of an image with the distance for the coordinate represented, and calculates the visual range using the image pattern recognition method.

2. A method for measuring a visual range using geometrical information of an image and an image pattern recognition method, the visual range measurement method comprising:

receiving an image from an IP camera installed in a measurement site;

performing distance-mapping on the analytic region of the received image;

determining an image visual range function from the received image;

applying an image pattern recognition method using ambient color information of an object from the received image; and calculating a visual range from a coordinate calculated by the image pattern recognition method, wherein determining the image visual range for calculating a visual range from a zero distance, a coordinate visual range, and a distance per y-coordinate of an object positioned furthermost in the analytic region of an image with the distance for the coordinate represented.

3. The method of claim 2, wherein performing the distance-mapping on the analytic region of the received image includes inputting geometrical information for a 2-dimensional plane coordinate from the received image to represent a distance.

4. The method of claim 2, wherein applying the image pattern recognition method using ambient color information of an object from the received image includes extracting RGB values of an ambient reference color of the object, setting a similar color tolerance range, and connecting similar colors in the tolerance range for the RGB values of the reference color to display an area.

* * * * *